Figure 1:
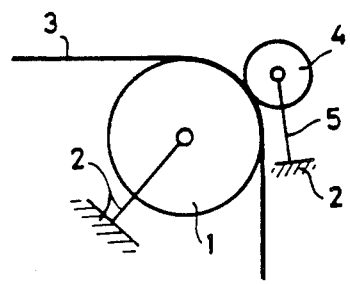

United States Patent [19]

Ravensbergen

[11] Patent Number: 4,877,332
[45] Date of Patent: Oct. 31, 1989

[54] TRANSDUCER FOR DETERMINING CONTAMINATIONS IN FABRICS

[75] Inventor: Wouter D. Ravensbergen, Leiderdorp, Netherlands

[73] Assignee: Yokogawa Electrofact B.V., Amersfoort, Netherlands

[21] Appl. No.: 207,048
[22] PCT Filed: Sep. 10, 1987
[86] PCT No.: PCT/NL87/00021
§ 371 Date: May 9, 1988
§ 102(e) Date: May 9, 1988
[87] PCT Pub. No.: WO88/02113
PCT Pub. Date: Mar. 24, 1988

[30] Foreign Application Priority Data

Sep. 18, 1986 [NL] Netherlands ............... 8602368

[51] Int. Cl.$^4$ ............... G01K 17/08; G01N 25/18
[52] U.S. Cl. ............... 374/153; 134/64 R; 374/59
[58] Field of Search ............... 73/159, 160; 324/62, 324/65 R; 374/43, 45, 169, 7

[56] References Cited

U.S. PATENT DOCUMENTS 3,207,125  9/1965  Strandberg, Jr. ............... 118/666
4,263,920  4/1981  Tasto et al. ............... 324/62 X
4,501,504  2/1985  Urmenyi et al. ............... 374/153 X
4,562,730  1/1986  Gowman ............... 73/159 X
4,638,346  1/1987  Inami et al. ............... 324/65 R X
4,714,874  12/1987  Morris et al. ............... 324/65 R

FOREIGN PATENT DOCUMENTS 2328963  5/1977  France.
55-71925  5/1980  Japan ............... 374/153

Primary Examiner—Daniel M. Yasich
Attorney, Agent, or Firm—Larson and Taylor

[57] ABSTRACT

A transducer is provided for determining the concentration of contaminants in fabric webs. The transducer includes an insulated measuring roller with two electrode rings separated by insulation and extending to the surface of the roller. The roller is supported on swing arms and the electrode rings are connected in the circuit of a conductivity meter. The swing arms cooperate with springs to provide for pressing of the roller against an insulated guiding roller for the fabric web under test. Additional metallic rings can be included in the roller which include temperature sensors used for compensating for the temperature dependency of the conductivity measurement. The guiding roller comprises a metallic roller with an insulating coating. Pairs of the rollers can be included in a device for washing fabric webs.

10 Claims, 2 Drawing Sheets

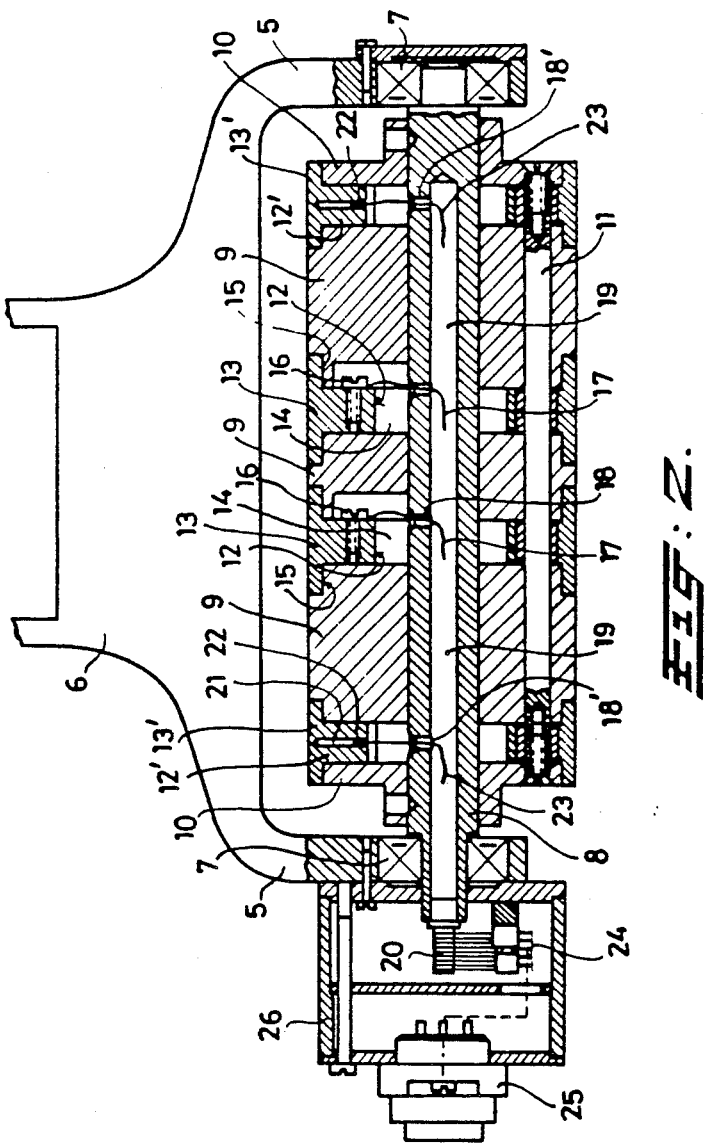

TRANSDUCER FOR DETERMINING CONTAMINATIONS IN FABRICS

When processing fabrics, the fabric webs are to be washed in a washing device, in order to remove therefrom excess chemicals, and in particular, alkaline substances, absorbed therein during processing.

Such a washing device consists of a plurality of washing basins, each being divided into compartments, in each of which a dip roller is arranged, and above said basins and between said dip rollers guiding rollers are provided, all this in such a manner that a continuous fabric web is guided alternately over a guiding roller and below a dip roller, and, thus, can be moved through the successive basins in which the fabric is contacted by washing water. This washing water is supplied to the last compartment of the last basin, is passed towards the preceding compartments and basins, and is, eventually, discharged from the first basin, so that the washing water flows in counter-current in respect of the fabric web. Before the first basin, between the various basins, and after the last basin, said web is moved between squeezing rollers in order to squeeze water therefrom, the water, in the case of the intermediate and last rollers, being returned again to the preceding compartment. Moreover said basins are provided with means for introducing steam into the washing water in order to heat the latter to the desired temperature.

When using such a washing device, there is a tendency to use too much washing water at a too high temperature, so as to ensure that the chemicals are well rinsed from the fabric. This leads to a useless energy and water consumption, also because, as the water is hotter, energy is lost in an increasing degree by evaporation, radiation and conduction. These energy losses might be substantially reduced if the washing effect could be measured in a dependable manner, since, then, it could be determined with which most economical amount of heat and/or water the desired washing effect could be obtained.

In the case of alkaline substances, or, in general, electrolytes such as salts, the conductivity of the wet fabric is a measure for the amount of electrolyte absorbed in the fabric. To that end measuring transducers have been designed, comprising electrodes to be contacted with the fabric, and included in the circuit of a conductivity meter. These measuring transducers have not been satisfactory, since, on the one hand, they influence because of friction the movement of the fabric web, and in particular may give rise to the formation of folds, which, for instance, can considerably interfere with a subsequent colouring or printing operation, and, on the other hand, fibre particles can be scraped from the fabric by said electrodes, which will accumulate on the electrode, and will, thereby, unfavourably influence the measurement result.

The invention provides a transducer means for this purpose which does not show the above-mentioned objections, and which, to that end, is characterised by a measuring roller of insulating material, in which two electrode rings which are mutually separated by an insulating interspace are included, which rings smoothly join the insulating surface of said roller, which roller is rotatably supported in swinging arms or the like, the rotation axis of said roller being provided with slip rings, by means of which the measuring electrodes can be included in the measuring circuit of a conductivity meter, which roller is adapted to be pressed, by means of springs acting on said swinging arms or the like, with a well-determined force against a guiding roller for guiding the fabric web to be examined, which guiding roller is provided with an insulating surface.

Since the measuring roller is uniformly pressed against the guiding roller, and rotates together with said guiding roller when the fabric web is passing, no friction forces giving rise to the formation of folds or the like will be exerted on said fabric web, and accumulation of fabric particles will not take place either, and fabric particles possibly adhering to said measuring roller can be easily removed therefrom during operation.

For a practical operation of this transducer, a distance between the electrode rings of about 5 mm and a width of said electrode rings of about 20 mm has appeared to be favourable.

In order to avoid polarisation effects, the measuring circuit of the conductivity meter is operated with alternating current, which, preferably, has a frequency of 2 kHz or more, since it has appeared that at lower frequencies linearity deviations will occur.

At a distance from said electrode rings one or more metal rings which smoothly join the roller surface can be included in the measuring roller, each of said rings being provided with one or more electrical temperature measurement elements, and the measuring elements of at least one of said rings can be adapted for producing a signal which is suitable for compensating the temperature dependency of the conductivity measurement.

The outer surface of the rings included in the measuring roller should be corrosion-proof, to which end said rings will be manufactured from stainless steel and/or can be provided with a coating of a precious metal.

The guiding roller for guiding the fabric web can be a metallic guiding roller which is provided with an insulating coating, in particular a shrinkable hose of polyethene or the like.

The invention relates, furthermore, to a device for treating and to in particular, washing fabric webs, and is characterised in that, at the input and output ends of said device, a measuring transducer of the above-mentioned kind is arranged, and in that the measuring circuits connected to said transducers are adapted to compare the measuring signals of both transducers with one another. In particular the guiding roller of each transducer can be a guiding roller forming part of the processing device.

Figure 3:
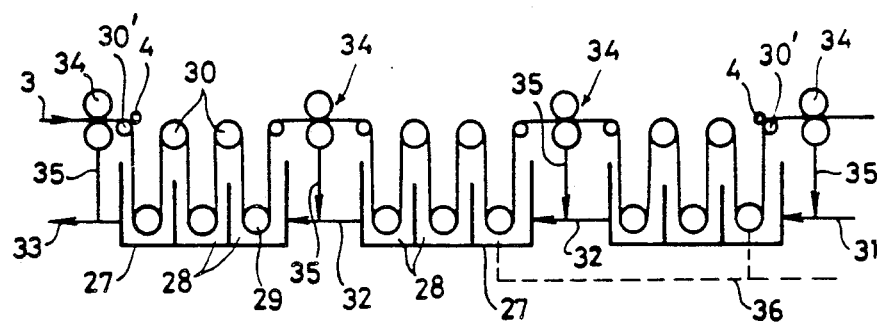

The invention will be elucidated below by reference to a drawing, showing in:

FIG. 1 a diagrammatical lateral view of a measuring transducer according to the invention;

FIG. 2 an axial cross-section at a larger scale of the measuring roller of said transducer; and FIG. 3 a diagrammatical representation at a highly reduced scale of a washing device with two transducers according to the invention.

In FIG. 1 a transducer means according to the invention is schematically shown. This transducer means comprises a guiding roller 1, which is rotatably supported on a supporting frame 2 schematically shown, and which is provided with an insulating surface contacting a fabric web 3 passing by to be examined.

At the other side a measuring roller 4 of the transducer means bears on the web 3, which roller 4 is pressed, by means of adjustable leaf springs mounted on the frame 2 or by corresponding swing arms 5 under an adjustable spring load, against the guiding roller 1. Care should be taken to provide good parallelism of the rotation axes of the rollers 1 and 4, in order to ensure a uniform contact between the measuring roller 4 and the fabric web 3 supported on the guiding roller 1.

FIG. 2 shows a practical embodiment of the measuring roller 4 of FIG. 1. Therein the arms 5 are connected with a yoke 6 which is supported on a swing axis not shown, and is provided with spring means not shown. The arms 5 each carry a ball bearing 7 in which a hollow shaft 8 is rotatably supported. On this shaft 8 three insulating discs 9 are provided which, by means of end plates 10 and if required, tensioning bars 11, are kept together.

Between the discs 9 two conducting electrode discs 12 with widened outer rings 13 are clamped, which discs have a central hole 14 providing a clearance in respect of the shaft 8, said rings 13 fitting in recesses 15 of the insulating discs 9, and the outer surfaces of said rings 13 smoothly join the outer surfaces of the discs 9.

Each electrode disc 12 is, by means of a terminal screw 16, connected to a measuring wire 17 which is led through a corresponding hole 18 in the shaft 8 towards the bore 19 thereof. Said wires are, on the other hand, each connected to a corresponding slip ring 20 which is mounted at one end of the shaft 8 beyond the ball bearing 7.

Between the outermost insulating discs 9 and the adjacent end discs 10, two additional conducting discs 12' with outer rings 13' are provided which mainly correspond to the electrode discs 12, but are provided with a bore 21 in which a temperature sensor 22 is arranged, which sensors are connected, by means of corresponding wires 23 which are led through a transverse hole 18' towards the bore 19 of the shaft, to corresponding slip rings 20. These temperature sensors 22 serve for determining the temperature of the fabric web 3.

Brushes 24 contact the slip rings 20, and are connected to corresponding contact pins or bushes of a connecting box 25 which is, in turn, connected to a conductivity measurement circuit including a conductivity meter indicated at CM. The slip rings 20 and the brushes 24 are included in a water-proof housing 26.

The electrode discs 12 are to be included in the measuring circuit of a conductivity meter, and one of the temperature sensors 22 is used for producing a signal for compensating the influence of the temperature on the conductivity, which signal is supplied to the conductivity meter. The other sensor 22 can be used for indicating the temperature of the fabric if this would be needed. It is also possible to use both sensors 22 for temperature measurement, if an average value over the width of the web is desired, and also more than one temperature sensor 22 can be provided in each ring 12'.

When the measuring roller 4 is contacted with the wet web 3, a current will flow from the current source via the respective slip rings 20 and electrode rings 13 towards the intermediate wet fabric portion, the intensity thereof being related with the concentration of the contaminants in the web 4, and in particular alkaline substances or salts. This current source should be an alternating current source in order to avoid polarisation, and it has appeared that below a frequency of about 2 kHz the linearity of the measurement decreases. The electrode rings 13 should have a sufficient width in order to obtain a good contact with the fabric, and it has appeared that a width of about 20 mm is suitable. The distance between the inner edges of said electrode rings 13 should not be too large or too small, 5 mm has appeared to be a suitable value.

The rings 13 and 13' should be corrosion-proof in order to ensure a dependable measurement result. These rings can be made, for instance, of stainless steel, and/or be provided with a coating of a precious metal, in particular gold. The insulating rings 9 consist of a suitable plastics.

FIG. 3 shows in a diagrammatical manner a current washing device. This device consists of a plurality of basins 27, each being divided by means of partitions into compartments 28. In each compartment 28 a dip roller 29 is arranged, and above said basins guiding rollers 30 are mounted in such a manner that a fabric web 3 can be led, in the manner shown, through the consecutive compartments, in which compartments said web is contacted with washing water.

The water is supplied at 31 to the last compartment of the last basin, and flows through connections 32 towards preceding basins, and the first compartment of the first basin communicates with a discharge duct 33. Before, between or behind said series of basins pressure roller pairs 34 are arranged by means of which water present in the web can be squeezed, said water being returned to the water flow by means of ducts 35 as shown.

As shown two guiding rollers 30' at the input side of the first basin and, respectively, the output side of the last basin, are constructed as a guiding roller 1 of a transducer means of the kind described above, each guiding roller being in contact with a measuring roller 4. Said rollers 30' form a part of the washing device, but should, for the present purposes, be provided with an insulating coating, and, for instance, a shrinkable hose can be shrunk on these rollers to that end.

By means of both transducers means 4 of FIG. 3, the contamination content giving rise to conductivity variations can be measured before and after the washing treatment, from which the washing effect can be derived. To that end a difference or ratio measurement can be used, by means of which a signal can be obtained that can be used for controlling the water flow or of the steam supply schematically indicated at 36 by means of which the temperature of the washing water in the various basins can be brought to the desired value. Then the price of steam and water can be taken into account, in order to compute the most favourable solution for obtaining the desired washing effect.

Since the measuring transducers of the kind mentioned above are contacting the fabric web in a relatively small surface area, which surface, moreover, depends on the pressure exerted on the measuring roller and the character of the fabric, the so-called cell constant of such a transducer means (A/1, in which A is the surface area, and 1 the length of a measuring cell) is difficult to be determined, but in the case of comparative measurements with two cells this constant is of no importance, if both transducers produce, under the same circumstances, the same signal.

I claim:

1. A transducer for use in apparatus for determining the concentration, in fabrics, of contaminants in the fabrics which affect the conductivity of the fabrics, wherein said transducer contacts a web of fabric being tested and produces an output signal related to the conductivity of the fabric and wherein said apparatus includes a measuring circuit, including a conductivity meter, connected to said transducer, said transducer comprising a measuring roller made of insulating material including two electrode rings separated from each other by said insulating material and being disposed so as to smoothly join the insulating surface of said roller, said roller being rotatably supported by support means and including a rotation shaft provided with slip rings by means of which the electrode rings are connected in the measuring circuit of said conductivity meter, said transducer further comprising spring means acting on said support means for pressing said roller with predetermined force against a guiding roller for guiding the fabric web, said guiding roller being provided with an insulating surface.

2. The transducer of claim 1, wherein the distance between the electrode rings is about 5 mm, and the width of the electrode rings is about 20 mm.

3. The transducer of claim 1, wherein the conductivity meter operates with an alternating current of 2 kHz or more.

4. The transducer of claim 1 wherein said roller further comprises at least one additional metallic ring disposed so as to smoothly join the roller surface said at least one additional ring being provided with at least one electric temperature measuring element.

5. The transducer of claim 4, wherein said at least one measuring element of said at least one additional ring comprises means for producing a signal for compensating for the temperature dependency of a conductivity measurement made by said measuring circuit.

6. The transducer of claim 1, wherein said rings are made of stainless steel.

7. The transducer of 1 wherein the guiding roller for guiding the fabric web comprises a metallic guiding roller provided with an insulating coating, in particular shrinkable hose of polyethene or the like.

8. The transducer of claim 1 wherein said rings are provided with a coating of a precious metal.

9. An apparatus for determining the concentration, in fabrics, of contaminants in the fabrics which affect the conductivity of the fabrics said apparatus including a transducer which contacts a web of fabric being tested and which produces an output signal related to the conductivity of the fabric, and a measuring circuit, including a conductivity meter, connected to said transducer, the improvement wherein said transducer comprises a measuring roller made of insulating material including two electrode rings separated from each other by said insulating material and being disposed so as to smoothly join the insulating surface of said roller, said roller being rotatably supported by support means and including a rotation shaft provided with slip rings by means of which the electrode rings are connected in the measuring circuit of said conductivity meter, said transducer further comprising spring means acting on said support means for pressing said roller with predetermined force against a guiding roller for guiding the fabric web, said guiding roller being provided with an insulating surface.

10. A treatment device for treating fabric webs comprising an input end, an output end, and first and second measuring transducers, located respectively at said input end and said output end, for determining the concentration of contaminants in the fabric webs which affect the conductivity of fabric webs, each said transducer contacting a web of fabric being tested and producing an output signal related to the conductivity of the fabric and said transducers being connected in a measuring circuit including a conductivity meter, each said transducer comprising a measuring roller made of insulating material including two electrode rings separated from each other by said insulating material and being disposed so as to smoothly join the insulating surface of said roller, said roller being rotatably supported by support means and including a rotation shaft provided with slip rings by means of which the electrode rings are connected in the measuring circuit of said conductivity meter, each said transducer further comprising spring means acting on said support means for pressing said roller with predetermined force against a guiding roller for guiding the fabric web, said guiding roller being provided with an insulating surface, and said measuring circuit including means for comparing the output signals produced by said first and second transducers.

* * * * *